United States Patent [19]
Helenick

[11] Patent Number: 6,141,801
[45] Date of Patent: Nov. 7, 2000

[54] THERMAL GLOVE

[75] Inventor: Susan M. Helenick, Issaquah, Wash.

[73] Assignee: Consumer Choice Systems, Inc., Bellevue, Wash.

[21] Appl. No.: 09/040,029

[22] Filed: Mar. 17, 1998

[51] Int. Cl.[7] .................................................. A41D 19/00
[52] U.S. Cl. ....................................... 2/159; 2/160; 2/162
[58] Field of Search ............................... 2/158, 159, 160, 2/161, 162, 164, 167, 910, 917; 62/259.2, 259.3, 530; 602/2, 14, 62, 64, 75; 607/111, 108, 114

[56] References Cited

U.S. PATENT DOCUMENTS

| | | | |
|---|---|---|---|
| 1,970,081 | 8/1934 | Eisendrath | 2/158 |
| 4,535,482 | 8/1985 | Spector | 2/160 |
| 4,543,671 | 10/1985 | Monk | 2/158 |
| 4,671,267 | 6/1987 | Stout | 128/156 |
| 4,742,579 | 5/1988 | Dunford | 2/160 |
| 4,756,311 | 7/1988 | Francis, Jr. | 62/530 |
| 4,964,402 | 10/1990 | Grim et al. | 128/80 |
| 5,035,003 | 7/1991 | Rinehart | 2/159 |
| 5,050,596 | 9/1991 | Walasek et al. | 128/381 |
| 5,214,799 | 6/1993 | Fabry | 2/161 |
| 5,350,418 | 9/1994 | Janevski et al. | 607/111 |
| 5,376,066 | 12/1994 | Phillips et al. | 602/64 |
| 5,415,624 | 5/1995 | Williams | 602/14 |
| 5,498,234 | 3/1996 | Martel et al. | 602/64 |
| 5,572,744 | 11/1996 | Reid, Jr. et al. | 2/158 |
| 5,983,396 | 11/1999 | Morrow et al. | 2/161.1 |

*Primary Examiner*—Michael A. Neas
*Assistant Examiner*—Gary L. Welch
*Attorney, Agent, or Firm*—Townsend and Townsend and Crew, LLP

[57] ABSTRACT

A thermal glove fitted to a human hand having integrated with a body of the glove a thermal, gel-filled pack. The gel pack includes a sealed bladder constructed of flexible, durable material resistant to heat and rupture. The bladder encloses a thermal gel adapted for repeated heating and cooling, such as by microwave exposure or refrigeration. The gel retains and transmits heat energy or cold to the hand of a wearer and is repeatably rechargeable. In preferred aspects of the invention, the gel pack is removably placed within a pocket integrated with the body of glove and adapted to removably receive the gel pack. The pocket may include a closure to secure the pack within the pocket. In other preferred aspects of the invention, a technical glove is provided incorporating a thermal gel pack and further providing a support cuff extending up the forearm of the wearer for comfort, prosthetic and/or injury preventive use by technical workers, such as computer users and laboratory workers.

17 Claims, 6 Drawing Sheets

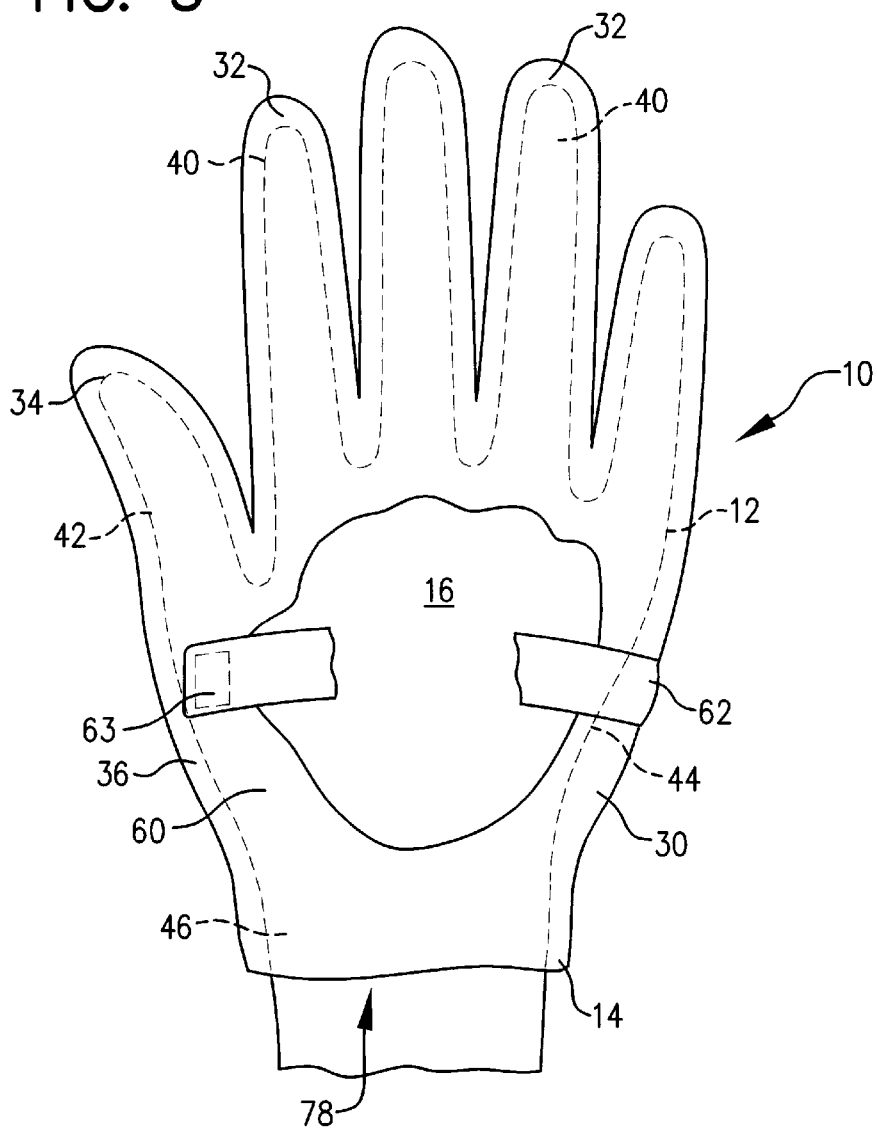
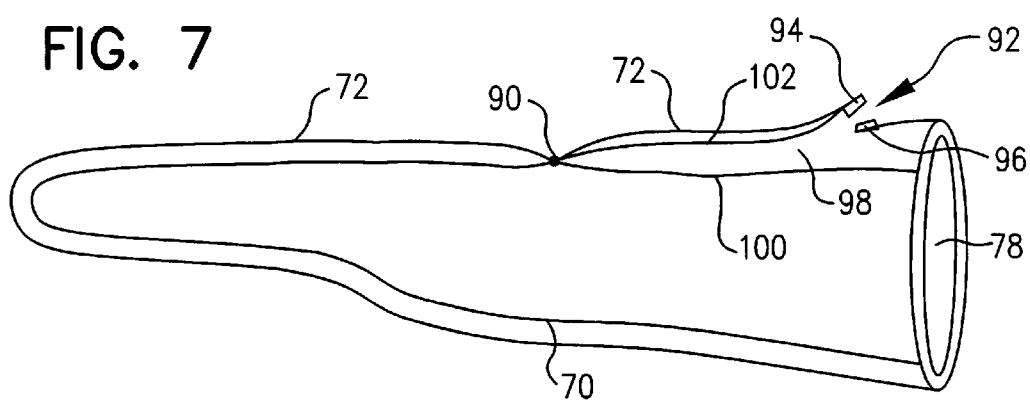

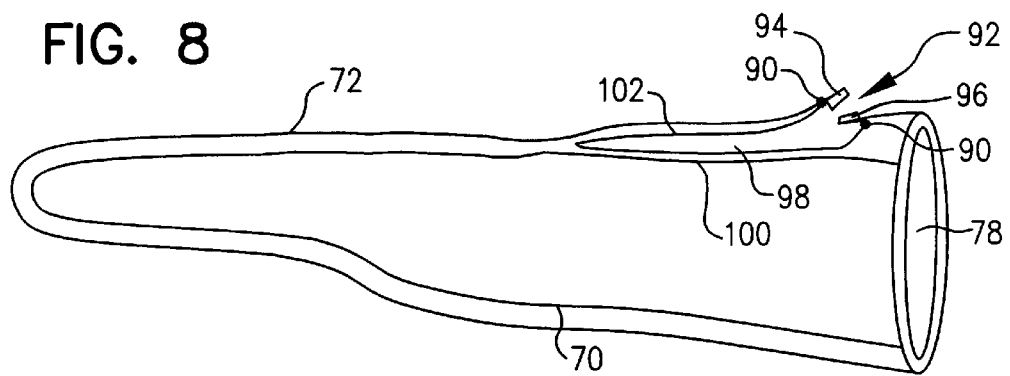
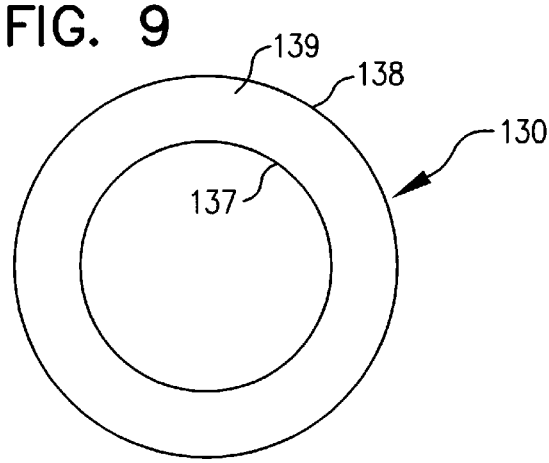
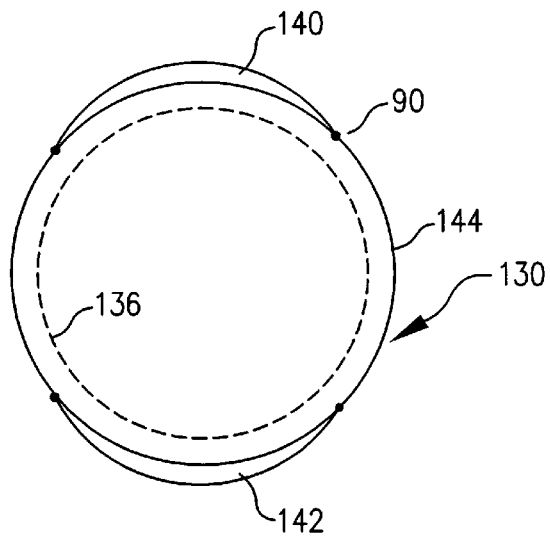
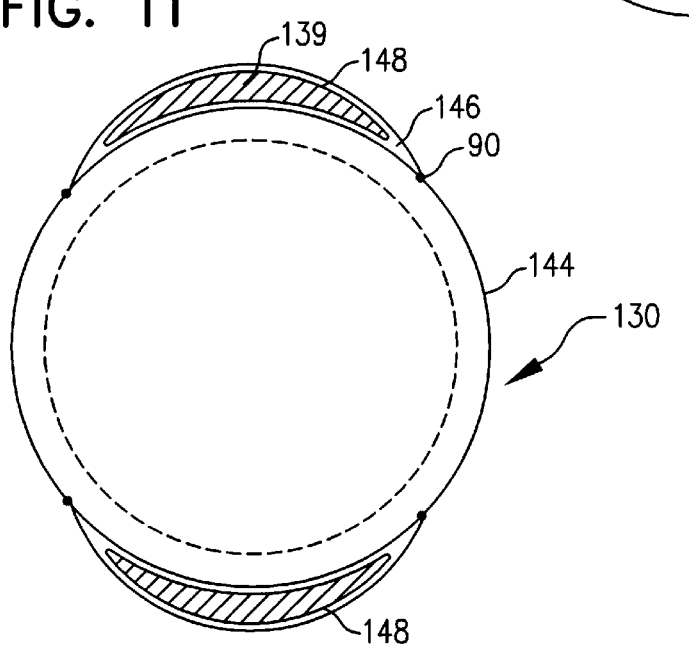

THERMAL GLOVE

TECHNICAL FIELD

The instant invention relates generally to gloves fitted to be worn on a human hand and, more specifically, to thermal gloves having a heating or cooling element integrated with a body of the glove for improved comfort.

BACKGROUND OF THE INVENTION

A variety of thermal glove and mitten designs have been proposed which incorporate a chemical, electric or fuel-burning heating element within the glove or mitten shell for warming the hands of the wearer. Examples of such gloves, which are generally designed for cold temperature, outdoor activities such as snow skiing, are described in U.S. Pat. No. 1,970,081 issued to Eisendrath on Aug. 14, 1934; U.S. Pat. No. 4,543,671 issued to Monk on Oct. 1, 1985; U.S. Pat. No. 4,535,482 issued to Spector et al. on Aug. 20, 1985; U.S. Pat. No. 4,742,579 issued to Dunford on May 10, 1988; and in U.S. Pat. No. 5,035,003 issued to Rinehart on Jul. 30, 1991.

Representative of these designs, Eisendrath (U.S. Pat. No. 1,970,081) discloses a thermal mitten having an inner lining and outer covering layer with a closeable pocket of waterproof material in between the inner and outer layers above the back hand portion of the glove. The pocket is designed to receive a chemical heating packet activated by wetting to impart heat to the hand of the wearer. In a comparable design, Monk (U.S. Pat. No. 4,543,671) discloses a thermal mitten having a closeable pouch formed in a lining of the mitten at the front (finger portion) or back hand portion of the mitten, the pouch being adapted to receive a heating element. In another comparable design, Dunford (U.S. Pat. No. 4,742,579) discloses a winter sports mitten having a heater pocket between an exterior face and inner glove lining of the mitten to receive a chemical heat pack.

In yet additional related designs, Rinehart (U.S. Pat. No. 5,035,003) and Spector et al. (U.S. Pat. No. 4,535,482) disclose thermal gloves heated by a chemical pack, or fuel-burning pocket warmer, respectively, contained within a pocket formed between inner and outer lining layers of the glove. Rinehart further discloses a liquid filled bladder coextensive with the glove lining, i.e., surrounding the palm and fingers, for distributing heat or cold generated by an exothermic or endothermic, chemical heat pack from the wrist portion of the glove to the extremities of the fingers. Spector et al. disclose a comparable design which uses strips of thermally conductive material extending along the thumb and fingers to distribute heat generated by a fuel-burning hand warmer throughout the hand, particularly to the vulnerable finger extremities.

Numerous problems attend the foregoing thermal glove and mitten designs. Among these problems is a typically heavy glove construction and bulky heat pack design which is poorly adapted for different environments and activities other than cold weather sports. Thus, these bulky designs may be poorly adapted for light activities such as walking and driving, or for indoor use such as in the work place.

In addition, each of the heat packs previously disclosed for use with gloves or mittens (including chemical, electrical and fuel-burning heat packs) all produce a more or less constant and uncontrollable level of heating or cooling energy, whereby a higher or lower level of heating or cooling cannot be selected by the user for maximum comfort suited to different environments and activities. Thus, these packs are again poorly adapted for use in different environments and activities ranging from cold outdoor sporting activities, to mild weather and light activity use, to indoor use such as in the work place. In the latter case, the non-adjustable heating capacity of prior art thermal gloves and mittens is not conducive to therapeutic uses of such devices in an indoor setting, e.g., to alleviate computer strain or other technical work-related strain such as that caused by laboratory work. In addition, each of the previously disclosed heat packs fails to provide a fast, repeatably rechargeable heating or cooling source, which is desired for long-term use, e.g., for long term therapeutic use during extended technical work activities.

In addition to the foregoing deficiencies, the construction of previously known thermal gloves and mittens is generally designed for manual shielding and thermal protection only. None of these gloves or mittens incorporate a therapeutic or prosthetic construction, e.g., a specifically adapted thermal design or, in addition or alternatively, a support element to alleviate orthopedic stresses such as those caused by prolonged computer use and other technical activities such as high tech and electronic assembly and laboratory work. Moreover, the bulky designs of previously known thermal gloves and mittens are ill-adapted for use in conjunction with such technical activities, which typically require unimpeded dexterity and tactile sensitivity.

Beyond the field of thermal gloves and mittens designed for cold outdoor sporting activities, a variety of therapeutic devices are known in the medical arts which feature a heating or cooling element, such as thermal gel-packs adapted to warm or cool injured portions of a patient's body. Thus, Stout (U.S. Pat. No. 4,671,267, issued Jun. 9, 1987) discloses an orthopedic therapy device featuring a body of thermal gel which can be heated or refrigerated to provide appropriate thermal treatment to an injured portion of a patient's body, e.g., an elbow, hand, or ankle. In one embodiment, Stout depicts an orthopedic wrap formed of stretch fabric with securing ties which encases a body of thermal gel, which wrap is designed for thermal treatment of body parts such as ankles, elbows and other joints. Alternatively, Stout discloses a thermal mitt for treatment of an injured hand, which mitt is bulky and features upper and lower, hand-shaped thermal gel bodies for warming or cooling the injured hand. The mitt is heated or cooled and then placed over a fabric glove which is pre-fitted onto the patient's hand. In a comparable disclosure, U.S. Pat. No. 5,050,596, issued to Walasek et al. on Sep. 24, 1991, teaches a bulky thermal mitt adapted to surround a patient's hand and provide heat or cold treatment thereto. Like Stout, Walasek et al. features a large gel body, coextensive with the outline of the palm and fingers.

As in the case of the outdoor thermal gloves and mittens, discussed above, numerous problems also attend the foregoing designs for therapeutic heat compresses and mitts, particularly in the context of activities other than immobile patient therapy. Again, the problem of heavy mitt construction and bulky heat pack design render these devices poorly adapted for different environments and activities other than treating injuries of an immobilized body part. In fact, these designs are poorly adapted for any active use, particularly any active use requiring unimpaired dexterity and tactile sensitivity such as computer use, assembly manipulation, and laboratory work.

In addition to the above described, outdoor thermal gloves and mitts and heat therapeutic wraps and mitts, previous designs are also disclosed for prosthetic wraps, splints and other supports to shield or immobilize body parts to treat and/or prevent injury. Thus, the prior art includes various wraps and splints that provide structural support for immobilizing or otherwise protecting such body parts as the hand, wrist or forearm. For example, a number of wraps and splints are specially designed for treating carpal tunnel syndrome caused by cumulative motion trauma, e.g., among grocery checkers. These supports are generally in the form of a partial brace conforming to the wrist and proximal half of the metacarpal portion of the hand, joined to a splint member extending up the forearm, which design limits repetitive impacts and vibrations affecting the wearer's wrist.

Other prosthetic devices are specially adapted to protect only the wearer's hand or specific parts thereof, and therefore do not extend to the wrist and/or forearm. One such device is disclosed in U.S. Pat. No. 5,350,418, issued to Janevski et al. on Sep. 27, 1994. This device is a splint having a rigid shell shaped to fit the center portion of the hand. The shell has a compressible gel pad attached to an inner surface thereof. The gel pad limits injury caused by external pressures or blows and also helps to desensitize incision sites and other trauma on the hand.

As in the case of the outdoor thermal gloves and mittens and heat therapeutic wraps and mitts, discussed above, prosthetic wraps and splints are also limited in terms of the range of environments and activities for which they may be used. In particular, these prosthetic devices generally lack a thermal construction or heating element, and are therefore not suited for outdoor or heat therapeutic activity. Likewise, these designs are poorly adapted for active use, because their general purpose is for immobilization or protection to prevent or treat injury. In this regard, prosthetic devices are particularly ill-suited for active use requiring unimpaired dexterity and tactile sensitivity, such as computer use, assembly manipulation, and laboratory work.

It is therefore an object of the present invention to provide a thermal glove which is well adapted for different environments and activities, including cold weather sports, light activities such as walking and driving, and indoor use such as for manual manipulative work.

It is an additional object of the invention to satisfy the above object in a thermal glove having a non-chemical, non-electrical and non-fuel-burning heat pack, and which incorporates a heat pack that produces a controllable level of heating or cooling energy, whereby a higher or lower level of heating or cooling can be selected by the user for maximum comfort suited to different environments and activities.

It is a related object of the invention to provide a thermal glove incorporating a heat pack having an adjustable heating capacity adapted to therapeutic uses associated with activities undertaken in an indoor setting, e.g., to alleviate computer strain and other technical work-related strain such as may be caused by laboratory work.

It is a further object that the heat pack incorporated within the thermal glove be adapted for fast, safe, and repeatable recharging suitable for long-term use, for example therapeutic use during extended technical work activities.

It is yet another object of the invention to provide a thermal glove satisfying the foregoing objects which also incorporates a therapeutic or prosthetic construction, e.g., having a specifically adapted thermal design for delivering heat or cooling to a specified portion of the user's hand, wrist and/or forearm, and optionally including a support element to alleviate orthopedic stresses such as may be caused by prolonged computer use and other technical activities.

It is still a further object of the invention to satisfy the foregoing objects in a thermal glove adapted for use in technical activities which require unimpeded dexterity and tactile sensitivity, such as computer use and laboratory work.

SUMMARY OF THE INVENTION

The present invention fulfills these and other objects and advantages by providing a glove fitted to a human hand having integrated with a body of the glove a thermal, gel-filled pack. Preferably, the glove is of a five digit design having the gel pack attached to or incorporated within a back hand portion of the body.

The gel pack includes a sealed bladder constructed of flexible, durable material resistant to heat and rupture. Sealably contained within the gel pack is a thermal gel adapted for repeated heating and cooling, such as by microwave exposure or refrigeration. The gel pack functions as a non-chemical, non-electrical and non-fuel burning heating element which retains and transmits heat energy or cold to the hand of a wearer and is repeatably rechargeable.

The gel pack may be attached to an outer surface of the glove body which is preferably of a single ply or double ply construction. When the glove body is of a double ply construction, the gel pack is preferably positioned between an inner, lining portion of the glove body and an outer, covering portion of the glove body. In more preferred aspects of the invention, the gel pack is removably placed within a pocket integrated with the glove body and adapted to removably receive the gel pack. The pocket generally conforms to the shape of the gel pack and may include a closure to secure the gel pack within the pocket. In more detailed aspects of the invention, the pocket and gel pack are fan shaped or multi-lobate to closely conform to a back hand outline of the glove body and provide other, novel advantages disclosed hereinbelow.

In one preferred embodiment of the invention, a technical glove is provided incorporating general aspects of the thermal glove described above and further providing novel structural features adapted for comfort, prosthetic and/or injury preventive use by technical workers, e.g., computer users, assembly workers, and laboratory technicians. The technical glove features, in addition to the basic thermal glove construction described above, a body made of a light weight, elastic material, with one or more fingertips of the glove removed for enhanced dexterity and tactile sensitivity. A support member of heavy or flex-resistant support material joins the glove body near a wrist portion thereof and extends rearward to supportively embrace a wrist and lower forearm of the wearer, thereby providing a novel support construction for alleviating computer strain and strain caused by other technical work activities. The support member may be in the form of a cuff that completely surrounds the wrist and lower forearm, or may be formed into upper and lower support bands joined along the sides of the forearm by a lighter, more flexible material. Preferably, the support member is a cuff that is cut longitudinally, e.g. in a V-shape, to adapt to forearms of different sizes among individuals, wherein opposing margins of the cuff can be overlapped and fixed relative to one another (e.g., by one or more closeable straps) by the wearer to snugly embrace the forearm for improved support. The support member may be fixedly attached to the glove body, eg., by stitching, or may be removably attached to the body, eg., by a hook-loop fastener or snaps.

In another preferred embodiment of the invention, a sport glove is provided incorporating general aspects of the thermal glove described above and further providing novel structural features adapted for sporting activities, e.g., biking, golf, skiing, racquetball and the like. Generally, the sport glove features a heavy construction of at least the outer, covering portion of the body, e.g., a layer of suede, leather or synthetic material of like strength and durability, and the finger tips are enclosed. Otherwise, the sport glove is comparable in design and construction to other gloves adapted to specific sports and well known in the art.

In yet another preferred embodiment of the invention, a light activity glove is provided incorporating general aspects of the thermal glove described above and further providing novel structural features adapted for light activities, e.g., walking and driving. Generally, the light activity glove features an intermediately heavy construction of the outer, covering portion of the body, e.g., a layer of calf skin, deer skin, or synthetic material of like strength and durability, and the finger tips are enclosed. Otherwise, the light activity glove is comparable in design and construction to other gloves adapted to specific light activities and well known in the art.

These and other aspects of the invention and their attendant objects and advantages will become apparent from the description which follows read in conjunction with the appended drawings. However, the following description and drawings are illustrative only, and that it will be readily apparent to the practitioner of ordinary skill in the art that changes can be made in the specific embodiments illustrated and described herein within the scope of the appended claims.

BRIEF DESCRIPTION OF THE DRAWINGS

FIG. 3 is a top plan view of a thermal glove according to the invention having a single ply body construction and an externally attachable gel pack.

FIG. 7 is a longitudinal, sectional view of a thermal glove according to the invention showing another alternative pocket construction.

FIG. 8 is a longitudinal, sectional view of a thermal glove according to the invention showing yet another alternative pocket construction.

FIG. 9 is a transverse, sectional view of a support cuff portion of a technical, thermal glove according to the invention.

FIG. 10 is a transverse, sectional view of an alternative support cuff portion of a technical, thermal glove according to the invention.

FIG. 11 is a transverse, sectional view of another alternative support cuff portion of a technical, thermal glove according to the invention.

DESCRIPTION OF THE SPECIFIC EMBODIMENTS

Figure 1:
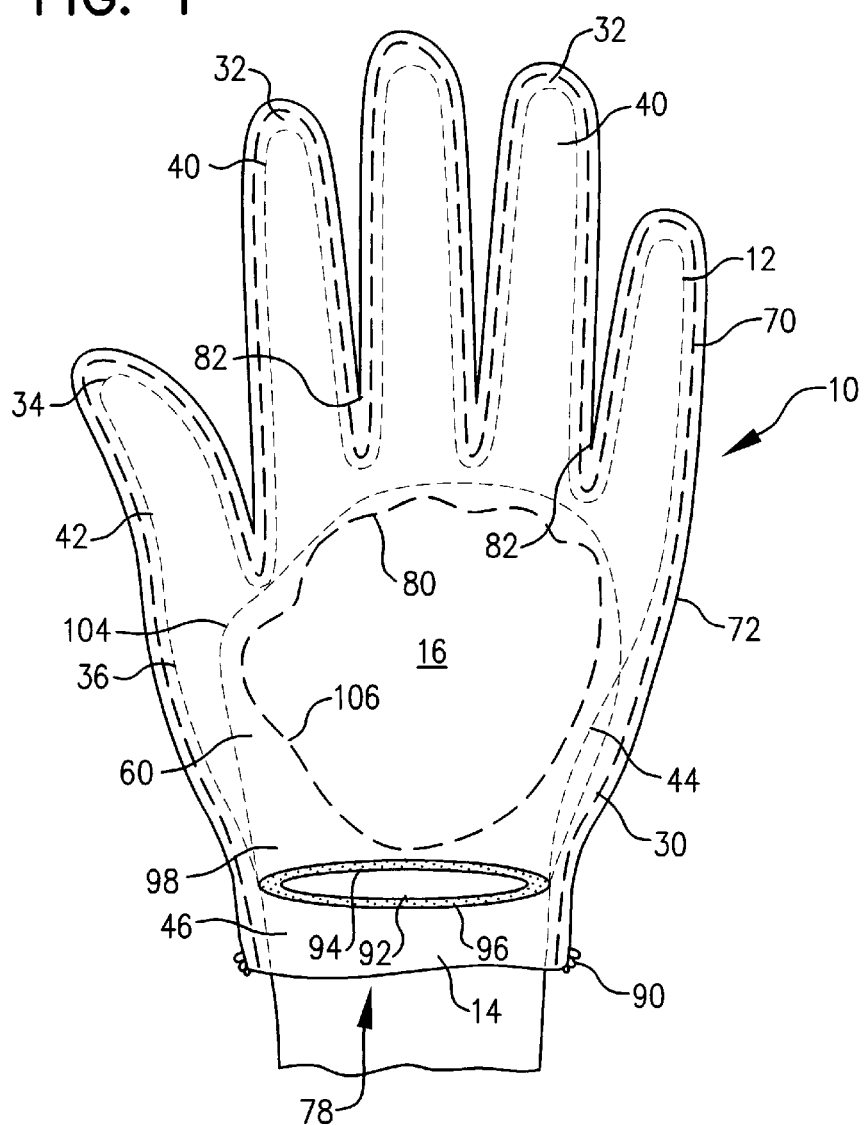
FIG. 1 is a top plan view of a thermal glove according to the invention.
Figure 2:
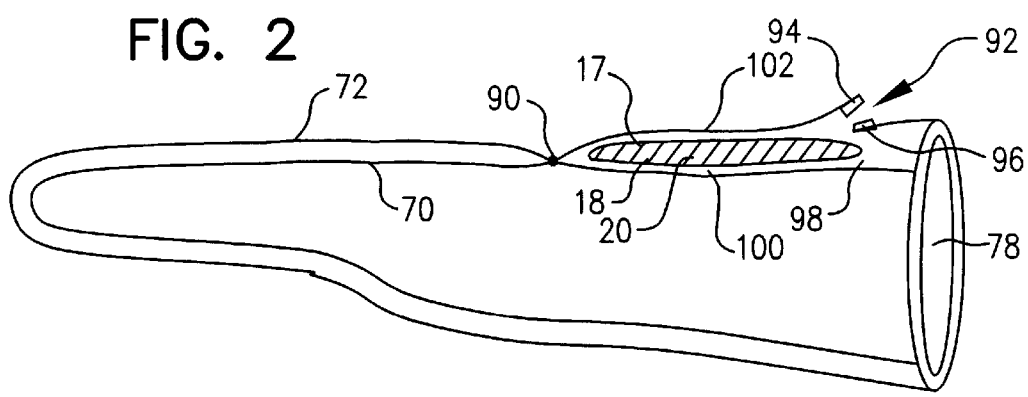
FIG. 2 is a longitudinal, sectional view of a thermal glove according to the invention.

As noted above, the instant invention provides a glove 10 fitted to a human hand 12 having integrated within or attached to a body 14 of the glove a thermal, gel-filled pack 16 (see FIG. 1). Referring to FIG. 2, the gel pack includes a sealed bladder 17 constructed of flexible, durable material resistant to heat, cold, and rupture. The gel pack bladder sealably contains within a lumen 18 of the bladder a thermal gel 20 adapted for repeated heating and cooling, for example by microwave exposure, immersion in hot or cold liquids, or refrigeration.

As shown in FIG. 3, the glove body 14 may be of a single ply construction, such as is found in conventional glove liners. Thus, a single ply shell 30 is provided which defines fitted finger pockets 32, a thumb pocket 34, and a metacarpal pocket 36, respectively sized and dimensioned to comfortably and snugly receive fingers 40, thumb 42 and a metacarpal portion 44 (i.e., including palm and backhand) of the hand 12 of a human subject of a pre-determined glove size (e.g., selected from small, medium or large, male or female glove sizes). The shell may optionally extend proximally beyond the metacarpal portion of the hand to cover a wrist, or carpal, portion 46 of the hand. The shell may be constructed from a variety of materials, such as cotton, nylon, wool, polypropylene, SPANDEX® or other natural or synthetic fibers of similar texture and flexibility commonly used in the textile industry. Preferably, the shell is thin, e.g. 1–5 mm and more preferably 3–4 mm, in uncompressed thickness, to provide comfort along with good flexibility and tactile sensitivity. Selection of materials, weaves, and shell thicknesses will also depend on insulation requirements, whereby the shell must provide for effective transmission of heat from the gel pack 16 across the shell to the hand 12, while at the same time insulating the wearer against discomfort or burns due to excessive heat transmission. Thus, for example, preferred shell materials, weaves and thicknesses allow for placement of the gel pack directly against an outer surface 50 of the shell when the gel pack is heated to a temperature of approximately 90° C., and provide an insulative layer such that heat transmitted through to an inner surface 52 of the shell generates an apparent temperature against the skin of the hand which does not exceed approximately 75° C. All of the materials which are incorporated in the glove body are preferably washable in conventional laundry treatments, and are also microwavable or otherwise heatable, eg., by immersion in hot water. When a support member is fixedly joined to the glove body (see below), it is also preferably made of machine washable, microwavable and heatable material. However, when the support member is removably joined to the body it can be made of alternative materials, eg., neoprene which may not be stable to all of the foregoing conditions but can be removed from the body prior to exposure of the body to such conditions, eg., microwave heating.

The shell is manufactured according to standard glove making methods, e.g., by cutting one or more sheets of selected shell material into an approximate hand-shaped pattern, and annealing cut edges where appropriate, such as by gluing or stitching, in accordance with conventional glove making methods.

For use in conjunction with the single ply glove shell 30, described above, the gel pack 16 may be adapted for removable attachment to a back hand surface 60 of the shell. Thus, in one preferred embodiment the gel pack is provided with an attachment device in the form of straps 62 adapted to securely engage the back hand surface of the shell, e.g., by having an underside surface of the straps invested with hooks as found in conventional hook-loop fasteners exemplified by VELCRO® hook-loop fasteners, which hooks engage the material of the shell or, alternatively, an opposing loop material 63 affixed to the shell. In this manner, the gel pack can be affixed to the back-hand surface of the glove after the gel pack has been heated to impart heat to the wearers hand and can be easily removed for re-heating by disengaging the straps and placing the gel pack in a heating environment, e.g., a microwave oven or container of hot water. Alternative devices to removably attach the gel pack to the glove shell are also contemplated, including for example conventional snaps and other well known attachment devices.

In a preferred embodiment of the invention, the glove body 14 is of a two-ply construction and the gel pack 16 is positioned between an inner, lining layer 70 and an outer, covering layer 72 of the glove body (see, e.g., FIGS. 1 and 2). The inner, lining layer closely is similar to the single ply shell 30, described above, in design, material, construction and function. Thus, the inner, lining layer defines fitted finger pockets 32, a thumb pocket 34, and a metacarpal pocket 36, respectively sized and dimensioned to receive the fingers 40, thumb 42 and metacarpal portion 44 of the hand 12. The inner, lining layer optionally extends to cover the carpal portion 46 of the hand. Also as in the case of the above described shell, the lining layer may be constructed from such conventional materials as cotton, nylon, wool, polypropylene, SPANDEX®, or other natural or synthetic fibers, and is thin, e.g., 1–5 mm and preferably 3–4 mm in uncompressed thickness. The inner, lining layer is also similar to the shell described above in terms of insulation function, i.e., it provides for effective transmission of heat from the gel pack 16 across the lining layer shell to the hand without discomfort or burns from excessive heat transmission.

Figure 4:
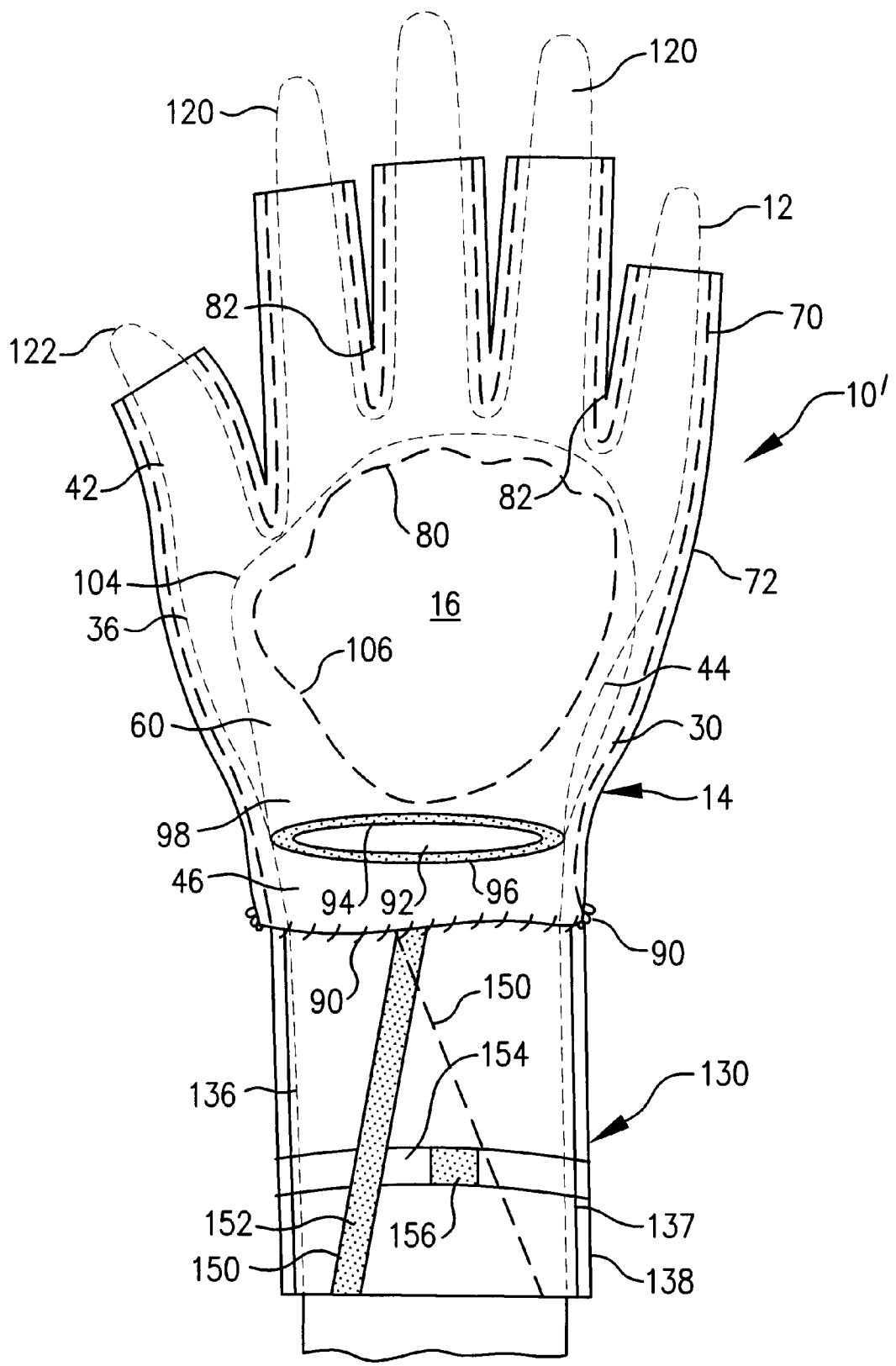
FIG. 4 is a top plan view of a thermal glove according the invention adapted for use by technical workers, combining both a thermal and prosthetic construction.

In the technical glove design, shown in FIG. 4, the entire glove body 14 (either a single ply body or an inner, lining layer 70 and outer, covering layer 72) is constructed of a light weight, elastic material, for example a stretch nylon, SPANDEX®, or other natural or synthetic fabric of like texture and flexibility, with each layer having a preferred thickness in the range of 1–3 mm, and more preferably about 2 mm for improved comfort and tactile sensitivity, subject to the above noted insulation requirements. Alternatively, in the sport glove design the outer, covering layer is specifically adapted for sporting activities, for example biking, golfing or skiing. Thus, the outer, covering layer of the sport glove features a heavy construction of, e.g., a 3–5 mm or greater thickness layer of suede, leather or synthetic material of similar strength and durability, comparable to standard covering materials used for gloves adapted to a particular sport of interest. In yet another alternative design, the light activity glove features an outer, covering layer of intermediate strength and thickness, for example a 2–4 mm thick layer of calf skin, deer skin, or synthetic material of like strength and durability, comparable to standard covering materials used for walking and driving gloves.

The outer, covering layer is shaped and dimensioned to cover and closely conform to the inner, lining layer, and thus defines similarly shaped, but slightly larger finger pockets, thumb pocket, and metacarpal pocket (not shown), and optionally extends to cover the carpal portion 46 of the hand. In one aspect of the two-ply glove design, the inner, lining layer 70 and outer, covering layer 72 are separate, similar to the design of a conventional glove liner and covering shell.

Figure 5:
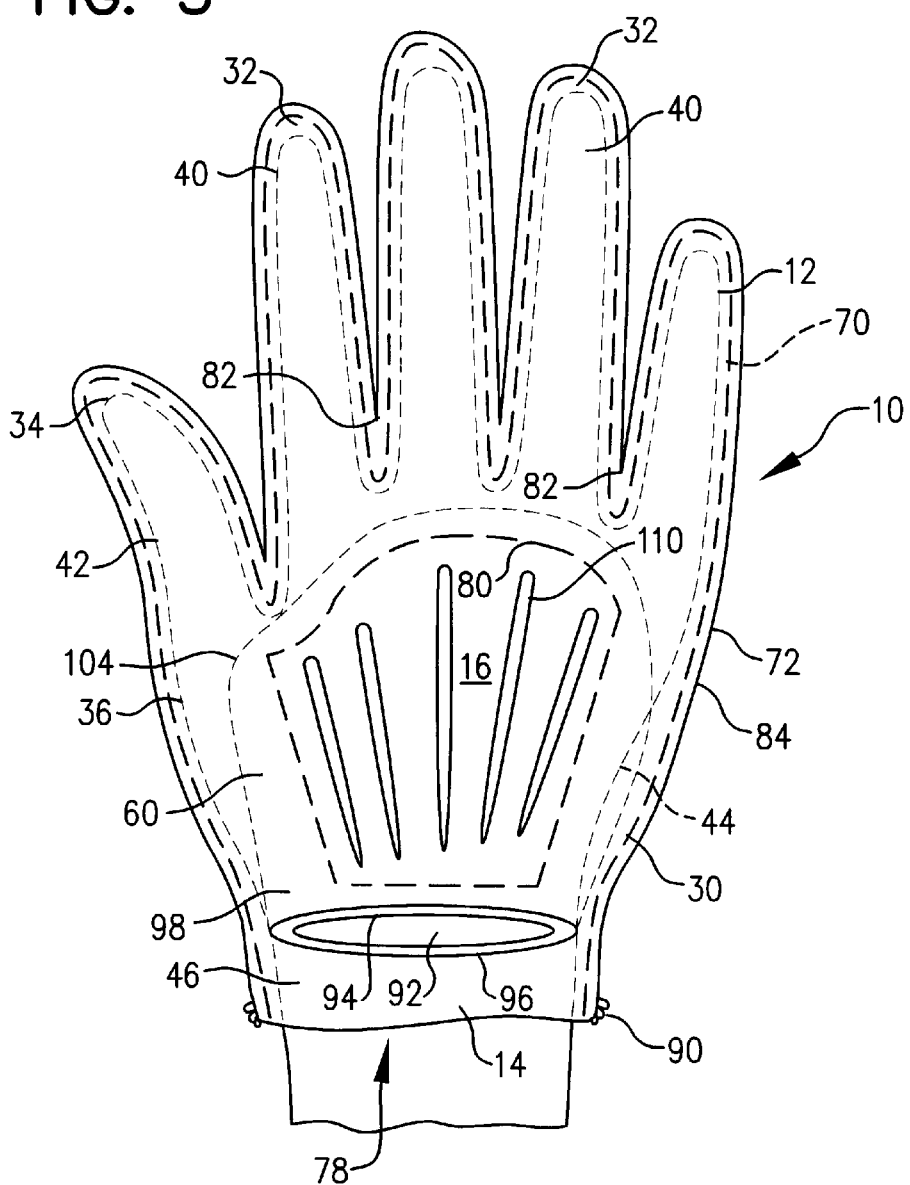
FIG. 5 is a top plan view of a thermal glove according to the invention having a two ply body construction and an integrated pocket for removable enclosure of the gel pack.

Thus, the inner, lining layer is placed on the hand 12 first, and the outer, covering layer is pulled on separately, over the lining layer. In this design, the gel pack 16 is simply inserted between the two layers at a proximal opening 78 of the glove body 14 where the hand is inserted. To insert the gel pack, the inner and outer layers are simply separated manually, and the gel pack is placed between the two layers and advanced distally (i.e., toward the tips of the fingers) so that the pack is positioned over the metacarpal portion 44 of the hand. In this context it is noteworthy that the shape of the gel pack can vary, e.g., from a square, rectangular, band, or circular shape. However, when the gel pack is to be thus inserted between separate layers of the glove body and positioned over the metacarpal portion of the hand, a square or circular shape is preferred so that the gel pack overlies a large area of the metacarpal portion for improved comfort and heating. Even more preferably, the gel pack can be generally fan shaped (i.e., having a distal end that is wider than a proximal end as shown in FIG. 5) or multi-lobate (as shown in FIGS. 1, 3 and 4) to more closely conform to an outline of the metacarpal portion of the hand and to provide other advantages, such as ease of insertion and positioning. In the latter context, it is notable that a forward edge 80 of the fan or multi-lobate gel pack is restrained from excessive forward and lateral movement by contact with interdigital vertices 82 and metacarpal sidewalls 84 of the outer, covering layer of the glove body, so that the gel pack does not shift position and interfere with comfort, joint flexure and dexterity (see FIG. 5). In conjunction with this two ply glove and novel shaped gel pack design it is therefore not necessary to provide any attachment device or pocket 98 to secure the gel pack in the desired position.

In more preferred aspects of the two-ply glove design, the inner, lining layer 70 and outer, covering layer 72 are joined, e.g., by stitching 90 through both layers around the proximal opening 78 of the glove body 14 in a conventional, unitary construction, two ply glove design. In this design, the gel pack 16 is removably inserted between the inner, lining layer and outer, covering layer through an access opening 92 in the outer, covering layer. As shown in FIGS. 1, 2 and 5, the access opening is preferably oriented transversely and is positioned slightly distal to the carpal portion 46 of the hand when the glove is being worn. Alternatively, the access opening may be oriented longitudinally above the midline or side of the back hand. The access opening is preferably closeable to secure the gel pack between the inner, lining and outer, covering layers, e.g., by having an upper margin 94 and lower margin 96 of the access opening opposingly faced with interlocking hook and loop material, e.g., VELCRO®, or closeable by other conventional closure means such as a zipper or snaps.

Figure 6:
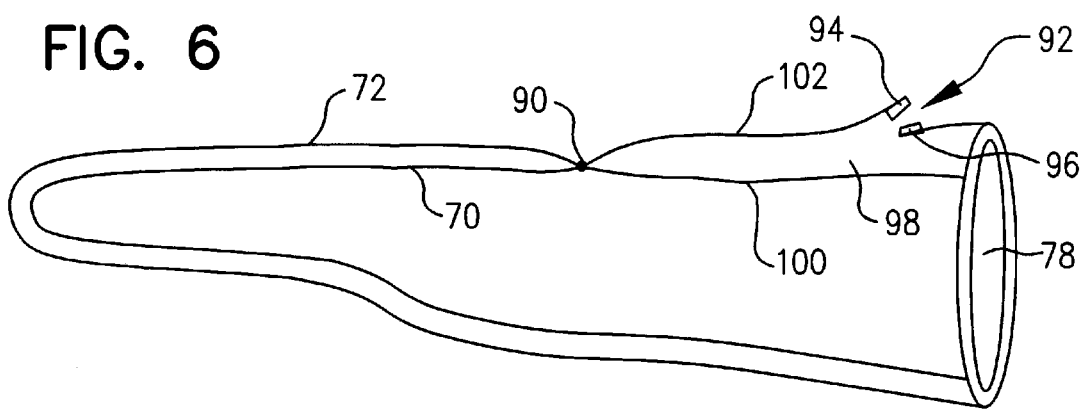
FIG. 6 is a longitudinal, sectional view of a thermal glove according to the invention showing an alternative pocket construction.

In yet another aspect of the invention, the gel pack 16 is inserted within a pocket 98 adapted to removably receive the gel pack. The pocket overlies the metacarpal portion 44 of the hand and may be formed separately from, or integral, to the inner, lining layer 70 and outer, covering layer 72 of the glove body 14. More specifically, as shown in FIGS. 2 and 6, the pocket may have a floor 100 formed by the inner, lining layer and a roof 102 formed by the outer, covering layer. In addition, the pocket may have a closed circumferential margin 104, as shown in FIGS. 1 and 5, this margin defined by annealing, e.g., by stitching 90 or gluing, the inner, lining layer and outer, covering layer together along an outline that roughly parallels a marginal outline 106 of the gel pack. Alternatively, as shown in FIG. 7, the pocket may be only partially integral to the glove body, having as its floor the inner, lining layer and having a separate layer as its roof 102 constructed of similar material as the inner, lining layer. In yet another alternative construction, the pocket may be entirely separate from the inner, lining layer and outer, covering layer, wherein the roof and floor of the pocket are continuous with each other and are anchored, e.g., by stitching 90, adjacent the upper margin 94 and lower margin 96, respectively, of the access opening 92, as shown in FIG. 8.

As in the case of the gel pack 16, the shape of the pocket 98 can vary, e.g., from a square, rectangular, band, or circular shape. Preferably, the pocket is square or circular in shape so that the gel pack overlies a large area of the metacarpal portion 44 of the hand for improved comfort and heating. Even more preferably, the circumferential margin 104 of the pocket roughly conforms to a fan shaped (FIG. 5) or multi-lobate (FIGS. 1, 3 and 4) marginal outline 106 of the gel pack to better hold the pack in position over the metacarpal portion of the hand.

With regard to construction of the gel pack 16, a preferred design for this aspect of the invention is a single layer bladder 17 constructed of flexible, durable material that is resistant to heat, cold, and rupture. Referring to FIG. 2, a lumen 18 of the bladder is filled with and sealably encloses a thermal gel 20 adapted for repeated heating and cooling. The bladder may be fabricated from a variety of materials having suitable flexibility, strength and durability to provide a supple, flexible feel when the gel pack is placed within the glove 10 and the glove is worn against the hand 12, and to be resistant to heat, cold, and rupture under the conditions of use specified herein. Suitable materials in this context include, for example, vinyl plastics, silicon plastics (e.g., silastic materials used for breast implants), latex or other like materials, provided the materials are heat stable and microwavable. It is particularly preferred that the material used to construct the gel pack bladder be expandable in order to allow for the escape of steam from the lumen of the bladder to the outside (i.e., through microscopic interstices in the bladder material) to prevent explosion of the bladder in the event of overheating.

In one exemplary embodiment of the invention, the gel pack bladder 17 is constructed of a vinyl or silicon plastic material cut into upper and lower sheets each having a marginal outline 106 corresponding generally to, but slightly smaller than, a circumferential margin 104 of the pocket 98. The two bladder sheets are annealed together, e.g., by gluing or heat sealing, along most of the marginal outline of the gel pack, leaving a small filling aperture between the two sheets for filling the bladder with gel 20. Gel is then protruded through the filling opening into the lumen 18 of the bladder formed between the two sheets, and the bladder is closed by heat sealing or otherwise annealing the two sheets together at the site of the filling aperture.

As noted above, the shape of the gel pack 16 can vary widely, although a preferred shape of the gel pack is fan shaped or multi-lobate. In addition, the gel pack can be of a variety of thicknesses, e.g., from about 3 mm to about 1 cm, and preferably about 4–6 mm in cross sectional thickness (FIG. 2). As shown in FIG. 5, the gel pack may also be reinforced with transverse or longitudinal ribs 110 to prevent buckling of the gel pack during insertion into the pocket, which ribs are generally oriented perpendicular to an orientation of the access opening 92 of the pocket 98.

The gel pack 16 functions as a non-chemical, non-electrical and non-fuel burning heating element which retains and transmits heat energy or cold to the hand 12 of the wearer. Notably, the gel pack has an adjustable heating capacity adapted to therapeutic and related uses associated with a range of activities, including recreational and technical activities undertaken in a cold environment (e.g., skiing, or technical activities such as forensic or marine studies, histopathological analysis, high tech repair and assembly, etc. undertaken in a cold-room environment), as well as for activities undertaken in an indoor setting that require a lower level of heating capacity from the gel pack. Briefly, the temperature and time period of heating or cooling of the gel pack dictates the level and duration at which the gel pack transmits heat or cold to the hand of the wearer, whereby a broad spectrum of heating levels and times can be selected by the user. The gel pack is further adapted for fast, safe, and repeatable heating or cooling, whereby the pack may be recharged repeatedly during long-term use, for example to provide continued therapeutic benefit during extended technical work activities.

A variety of gels are known in the art which are specifically adapted for their ability to be cooled and heated over a wide range of temperatures and to maintain their physical characteristics, e.g., chemical integrity and pliability, during repeated heating and cooling. Many such gels are suitable for use within the invention, while specific gel characteristics may be selected for use within different embodiments of the invention. Thus, gels having a higher maximum heating tolerance may be selected for use with outdoor sport gloves requiring a higher, longer term heating capacity than is desired for the light activity or technical glove. Alternatively, gels which maintain their physicochemical properties at very low temperatures may be selected for specific therapeutic uses, e.g., to reduce inflammation in a patient's hand following surgery. In most cases, however, it is generally desirable for safety purposes to select a gel having a wide range of temperature tolerance, e.g., from about −20° C. to about 160° C., to prevent decomposition of the gel or rupture of the gel pack bladder from exposure to low or high temperature extremes.

Gels of widely varying viscosities are known in the art and are generally useful within the invention. However, it is desirable to employ gels of different viscosities for use with different embodiments of the invention. In the case of the technical glove design disclosed herein, it is particularly desirable to employ a gel which is relatively soft (i.e., having a low viscosity, or firmness) when the gel pack is positioned over the metacarpal, i.e., back hand, region of the hand, so as not to unduly restrict dexterity or circulation of the wearer. Alternatively, firmer gels may be selected for incorporation within the support member of the technical glove to augment its support function.

Preferred gels for use within the invention include gels containing a water soluble humectant invested within a polymeric matrix (e.g., polymers, copolymers, or terpolymers containing monomer moieties, such as acrylic acid or acrylamide monomers). Suitable humectants include glycerin, dimethyl sulfoxide (DMSO), dimethyl formamide (DMF), among others. A preferred agent for the polymeric matrix is a commercially available acrylic acid polymer powder, e.g. Carbopol 940® (B.F. Goodrich Co.). Also included within the gel is a suitable cross-linking agent, for example, N,N methylene-bisacrylamide (MBA), N-methylolacrylamide, allyl methacrylate, or ethylene glycol dimethacryllate). Other agents are optionally included as well, such as initiators (e.g., $K_2S_2O_8$), anti-freeze/boiling point elevators (e.g., propylene glycol), absorbants (e.g., starch-acrylonitrile graft copolymers), agents to suppress bacterial growth, and/or agents to enhance processibility or shelf life.

It will be appreciated by persons skilled in the art that the consistency of the gel can be varied by selecting different polymeric materials and by varying the ratio of the polymer agent relative to the amount of humectant and/or cross-linking agent. To produce a soft gel the ratio of humectant to polymer should be high and/or a relatively low percentage of cross linking agent should be used. A firmer gel is produced by decreasing the humectant relative to polymer content and/or increasing the amount of cross-linking agent.

As noted above, the technical glove design disclosed herein may employ gel packs containing gels of different firmness depending on the location and purpose of the gel pack. A relatively soft gel is employed when the gel pack is positioned over the metacarpal region of the hand, for improved dexterity and circulation. An exemplary gel preparation for this purpose has a firmness range equivalent to the firmness range exhibited by test gel preparations having about 80% by weight glycerin, 10% by weight water, 10% by weight acrylamide, and between 0.01% and 0.10% by weight MBA. Another exemplary gel preparation for this purpose has a firmness range equivalent to a range of firmness exhibited by test gel preparations having about 80% by weight DMSO, 10% by weight water, and 10% by weight acrylic acid, and between 0.05% and 0.15% by weight MBA.

Firmer gels may be employed within the support member of the technical glove to augment its support function. An exemplary gel preparation for this purpose has a firmness range equivalent to a range of firmness exhibited by test gel preparations having about 80% by weight glycerin, 10% by weight water, 10% by weight acrylamide, and between 0.10% and 0.30% by weight MBA. Another exemplary gel preparation for this purpose has a firmness range equivalent to a range of firmness exhibited by test gel preparations having about 80% by weight DMSO, 10% by weight water, and 10% by weight acrylic acid, and between 0.15% and 0.65% by weight MBA.

In a preferred embodiment of the invention, a technical glove 10' is provided which incorporates general aspects of the thermal glove 10, described above, and further provides additional structural features adapted for comfort, prosthetic and/or injury preventive use by technical workers, including computer users, assembly workers, and laboratory technicians (see FIG. 4). The technical glove features a single ply or two ply body 14 with each layer (i.e., the single ply body or, alternatively, the inner, lining layer 70 and outer, covering layer 72) made of a light weight, elastic material as described above for the shell 30 and inner, lining layer 70. One or more fingertips 120 and/or a thumb tip 122 (corresponding to the distal most phalanges) of the glove body are removed for improved dexterity. Thus, in one embodiment an index finger tip is removed. Alternatively, the index finger tip and thumb tip may be absent. In yet another embodiment, all finger tips and the thumb tip are removed.

The technical glove features a support cuff 130 of heavy or otherwise flex resistant support material which joins the glove body 14 near the carpal portion 46 of the hand and is attached thereto, e.g., by circumferential stitching 90 (FIG. 4). The support cuff may be made of a variety of materials which provide prosthetic support, for example, neoprene, woven nylon (as used in ankle and wrist braces), or a strong, elastic wrap material such as is used in ace bandages. Alternatively, the support cuff may be formed of a non-supportive fabric and have integrated with the cuff support elements, such as structural rods, bands or ribs formed of a stiff material, for example metal, plastic, firm gel, and the like.

The support cuff 130 extends rearward (i.e., proximally) to supportively embrace the wrist and lower forearm 136 of the wearer to about a mid-forearm position (FIG. 4). In this manner, the support cuff provides prosthetic support to alleviate computer strain and other technical work strain. The supporting material of the support cuff 130 may completely surround the carpal portion 46 of the hand and lower forearm 136, as shown in FIG. 4. Thus, in one embodiment the support cuff is made of neoprene covered on an inner layer 137 and outer layer 138 with nylon, as found in conventional water sport suits. Alternatively, the support cuff may be constructed of nylon or other material having a weave and fiber orientation designed to restrict flexure of the wearer's wrist, for example as found in orthogonally woven nylon braces used for ankle and wrist support following injury. In yet another alternative embodiment, the support cuff includes an inner cuff layer 137 and outer cuff layer 138 surrounding a band of firm support gel 139 (which may also be heated) as described hereinabove (see FIG. 9).

In additional aspects of the invention, the support cuff 130 includes separate support elements, for example an upper support band 140 and lower support band 142 joined along the sides of the forearm 136 by connecting material 144 which is lighter or more flexible than the support bands (see FIG. 10). In one such embodiment, shown in FIG. 10, the connecting material forms a complete cuff surrounding the forearm, and upper and lower support bands are attached thereto, e.g., by stitching 90 or gluing. The support bands may be made of neoprene, e.g., a double nylon-sided neoprene. Alternatively, plastic, fiberglass, or metal rods, ribs or bands (e.g. ⅛ inch by 1 inch by 6 inch plastic or fiberglass bands running from the wrist up the forearm) may be affixed to the connecting material or enclosed within support pockets 146 affixed to the connecting material and sized and dimensioned to receive the rods, ribs or bands and hold them in a fixed position (see FIG. 11). In one such embodiment, shown in FIG. 11, the support bands are formed of support gel packs 148 containing a firm gel material 139 removably enclosed within the support pockets (e.g., by means of second and/or third, closeable access openings, not shown but similar to the first access opening described above located in the glove body). In this embodiment, the support gel packs are shaped and dimensioned to conform to a portion of the wearer's forearm 136, for example having an arcuate cross sectional shape, a width of about two inches and a length of about four to six inches. The support packs may also be removable to provide varying degrees of support, as well as for the purpose of heating the packs to provide therapeutic warming to the forearm and/or wrist of the wearer.

In preferred aspects of the invention, the support cuff 130 is cut longitudinally, e.g., in a V-shape, to adapt to forearms of different sizes among individuals (see FIG. 4). Opposing margins 150 of the cuff can thus be overlapped to adapt a circumference of the cuff to snugly fit forearms of different sized individuals. In this design configuration, the opposing margins of the cuff can be fixed relative to one another after they are overlapped by a number of closure devices, for example a marginal band 152 of hook material for engaging an opposite surface of fabric or loop material, or one or more closeable straps 154, eg., having a hook-loop closure 156 to close and open the strap, thereby firmly embracing the wearer's forearm for support.

Figure 12:
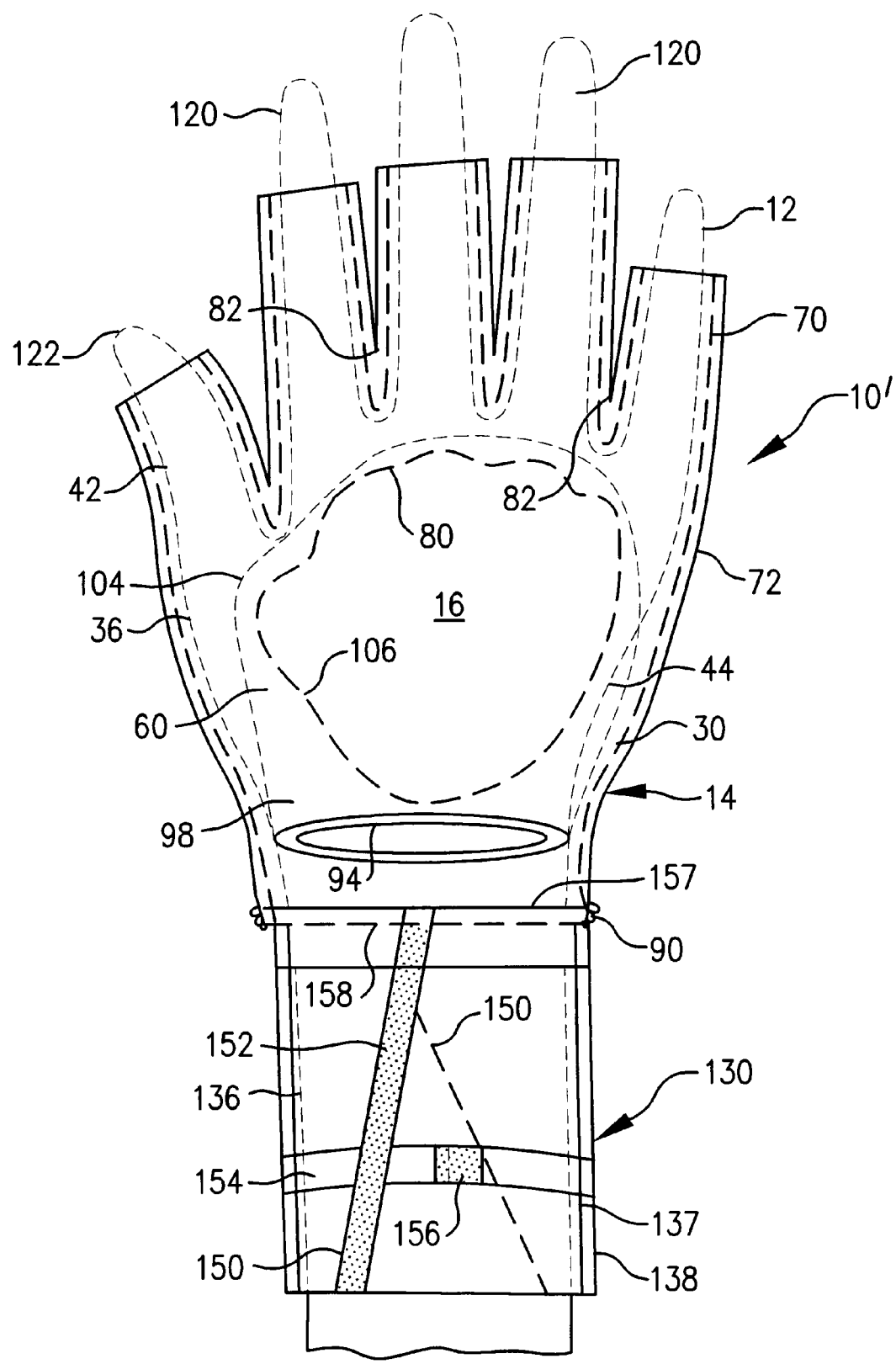
FIG. 12 is a top plan view of a thermal glove according the invention adapted for use by technical workers, combining both a thermal and prosthetic construction and featuring a support cuff that is removably attached to a body of the glove.

The support cuff 130 may be fixedly attached to the glove body 14, eg., by stitching, or may be removably attached to the body, eg., by a hook-loop fastener. Thus, in one preferred embodiment shown in FIG. 12, the support cuff is provided with an attachment device in the form of a marginal or circumferential attachment band 157 adapted to securely engage the glove body, e.g., by having an underside surface of the attachment band invested with hooks as found in conventional hook-loop fasteners exemplified by VEL-CRO® hook-loop fasteners, which hooks engage an opposing band 158 or opposing patches of loop material decorating the glove body 14, preferably near the carpal portion 46 of the hand. In this manner, the support cuff can be removably attached to the glove body after the body and/or gel pack 16 has been heated, and can be easily removed for alternative functionality of the glove body (i.e., to eliminate the support function but maintain other functionality of the glove) or for re-heating with the support cuff detached, by disengaging the hook-loop attachment. Alternative devices to removably attach the support cuff to the glove body are also contemplated, including for example conventional snaps and other well known attachment devices.

Although the foregoing invention has been described in some detail by way of illustration and example for purposes of clarity of understanding, it will be readily apparent to the artisan of ordinary skill that certain changes and modifications may be practiced within the scope of the appended claims.

What is claimed is:

1. A thermal glove fitted to a human hand comprising:
   a flexible glove body formed of a light weight, flexible material adapted for enhanced flexibility and tactile sensitivity of the wearer, the glove body defining finger pockets, a thumb pocket and a metacarpal pocket; and
   a thermal, gel-filled pack removably connected to a back hand portion of the glove body, said pack including a sealed bladder formed of a flexible, durable material resistant to heat and rupture and enclosing a thermal gel within a lumen of the bladder adapted for repeated heating and cooling; and
   a support cuff proximally attached to the glove body and adapted to extend up a forearm of a wearer for prosthetic and/or injury preventive use by technical workers, wherein the support cuff includes an inner cuff layer and an outer cuff layer surrounding a firm band of support gel.

2. A thermal glove fitted to a human hand comprising:
   a flexible glove body formed of a light weight, flexible material adapted for enhanced flexibility and tactile sensitivity of the wearer, the glove body defining finger pockets, a thumb pocket and a metacarpal pocket; and
   a thermal, gel filled pack removably connected to a back hand portion of the glove body, said pack including a sealed bladder formed of a flexible, durable material resistant to heat and rupture and enclosing a thermal gel within a lumen of the bladder adapted for repeated heating and cooling; and
   a support cuff proximally attached to the glove body and adapted to extend up a forearm of a wearer for prosthetic and/or injury preventive use by technical workers, wherein the support cuff includes separate support elements selected from the group consisting of neoprene bands, plastic, fiberglass, or metal rods, ribs or bands, and support gel packs.

3. The thermal glove of claim 1 or 2, wherein the gel pack is removably placed within a pocket integrated with the body of glove and adapted to removably receive the gel pack.

4. The thermal glove of claim 3, wherein the pocket includes a closure to secure the gel pack within the pocket.

5. The thermal glove of claim 1 or 2, wherein the support cuff is cut longitudinally and has overlappable, opposing margins and closure means to adjust a diameter of the cuff to adapt to forearms of different sizes among individuals.

6. The thermal glove of claim 1 or 2, wherein the support cuff is removably attachable to and detachable from the glove body.

7. The thermal glove of claim 1 or 2, wherein the support cuff is made of neoprene covered on an inner surface and outer surface with fabric.

8. The thermal glove of claim 1 or 2, wherein the support cuff is made of a prosthetic material having a weave and fiber orientation adapted to restrict flexure of a wearer's wrist.

9. The thermal glove of claim 1, wherein the support gel is heat and cold resistant to permit warming and cooling of the gel.

10. The thermal glove of claim 2, wherein the support cuff includes separate support elements that are removably enclosed within support pockets by a closeable access opening.

11. The thermal glove of claim 2, wherein the support cuff includes separate support elements that are support gel packs removably enclosed within support pockets, said gel packs having an arcuate cross section to conform to a portion of a wearer's forearm.

12. The thermal glove of claim 2, wherein the support cuff includes separate support elements that are support gel packs removably enclosed within support pockets, said support packs containing a firm gel for prosthetic support which gel is heat and cold resistant to permit warming and cooling of the gel.

13. The thermal glove of claim 1 or 2, wherein one or more of the finger and thumb pockets are open distally to expose one or more distal phalanges of a wearer for improved dexterity and tactile sensitivity.

14. The thermal glove of claim 1 or 2, wherein the glove body has a two ply construction and the thermal gel pack is positioned between an inner, lining layer and an outer, covering layer of the glove body.

15. The thermal glove of claim 1 or 2, wherein the glove body has a single ply shell construction and the thermal gel pack is attached to a back hand portion of the shell.

16. The thermal glove of claim 15, wherein the glove body has a single ply shell construction and the thermal gel pack is attached to a back hand portion of the shell by straps having an undersurface of hook material adapted to engage the shell or an opposing loop material affixed to the shell.

17. A thermal glove fitted to a human hand comprising:
   a glove body formed of a light, flexible material defining finger pockets, a thumb pocket and a metacarpal pocket, one or more of said finger pockets and thumb pocket being open distally to expose one or more distal phalanges of a wearer for improved dexterity and tactile sensitivity; and
   a thermal, gel-filled pack removably connected to the glove body, said pack including a sealed bladder formed of a flexible, durable material resistant to heat and rupture and enclosing a thermal gel within a lumen of the bladder adapted for repeated heating and cooling; and
   a support cuff proximally attached to the glove body adapted to restrict movement of a wrist joint of a wearer, wherein the support cuff incorporates a support gel having a different firmness compared to a firmness of said thermal gel.

* * * * *